United States Patent
Farley et al.

(10) Patent No.: US 7,309,321 B2
(45) Date of Patent: Dec. 18, 2007

(54) EMERGENCY MEDICAL COLLAR

(75) Inventors: Daniel K. Farley, Traverse City, MI (US); Richard Saunders, Etna, NH (US); Anthony J. Mulac, Traverse City, MI (US)

(73) Assignee: Spine Works, LLC, Traverse City, MI (US)

( * ) Notice: Subject to any disclaimer, the term of this patent is extended or adjusted under 35 U.S.C. 154(b) by 43 days.

(21) Appl. No.: 11/229,867

(22) Filed: Sep. 19, 2005

(65) Prior Publication Data

US 2007/0066922 A1    Mar. 22, 2007

(51) Int. Cl.
*A61F 5/00*    (2006.01)

(52) U.S. Cl. .................................................. 602/18

(58) Field of Classification Search ............ 602/17–18, 602/13; 128/DIG. 23, 845, 857, 870; 2/44, 2/45

See application file for complete search history.

(56) References Cited

U.S. PATENT DOCUMENTS

| | | | |
|---|---|---|---|
| 3,212,497 A | 10/1965 | Dickinson | |
| 3,745,998 A | 7/1973 | Rose | |
| 3,762,404 A * | 10/1973 | Sakita | ............................ 602/6 |
| 4,261,349 A | 4/1981 | Frosch et al. | |
| 4,657,003 A * | 4/1987 | Wirtz | ......................... 128/869 |
| 5,626,150 A | 5/1997 | Johnson et al. | |
| 5,718,669 A | 2/1998 | Marble | |
| 5,891,069 A * | 4/1999 | Moffett | ........................ 602/18 |
| 6,276,365 B1 | 8/2001 | Stelzenmuller | |
| 6,656,143 B2 | 12/2003 | Browd | |

* cited by examiner

*Primary Examiner*—Kim M. Lewis
(74) *Attorney, Agent, or Firm*—McAndrews, Held & Malloy, Ltd.

(57) ABSTRACT

An emergency medical collar adapted to be moved between a first more flexible state and a second more rigid state includes a body sized and adapted to be fitted to the neck region of a patient, and a chamber disposed inside of the body. The emergency medical collar also includes a support element disposed inside of the chamber. The emergency medical collar is adapted to allow attachment to the neck region of a patient when the neck of the patient is in a variety of positions, for example, neutral, extended, flexed, or lateral.

13 Claims, 5 Drawing Sheets

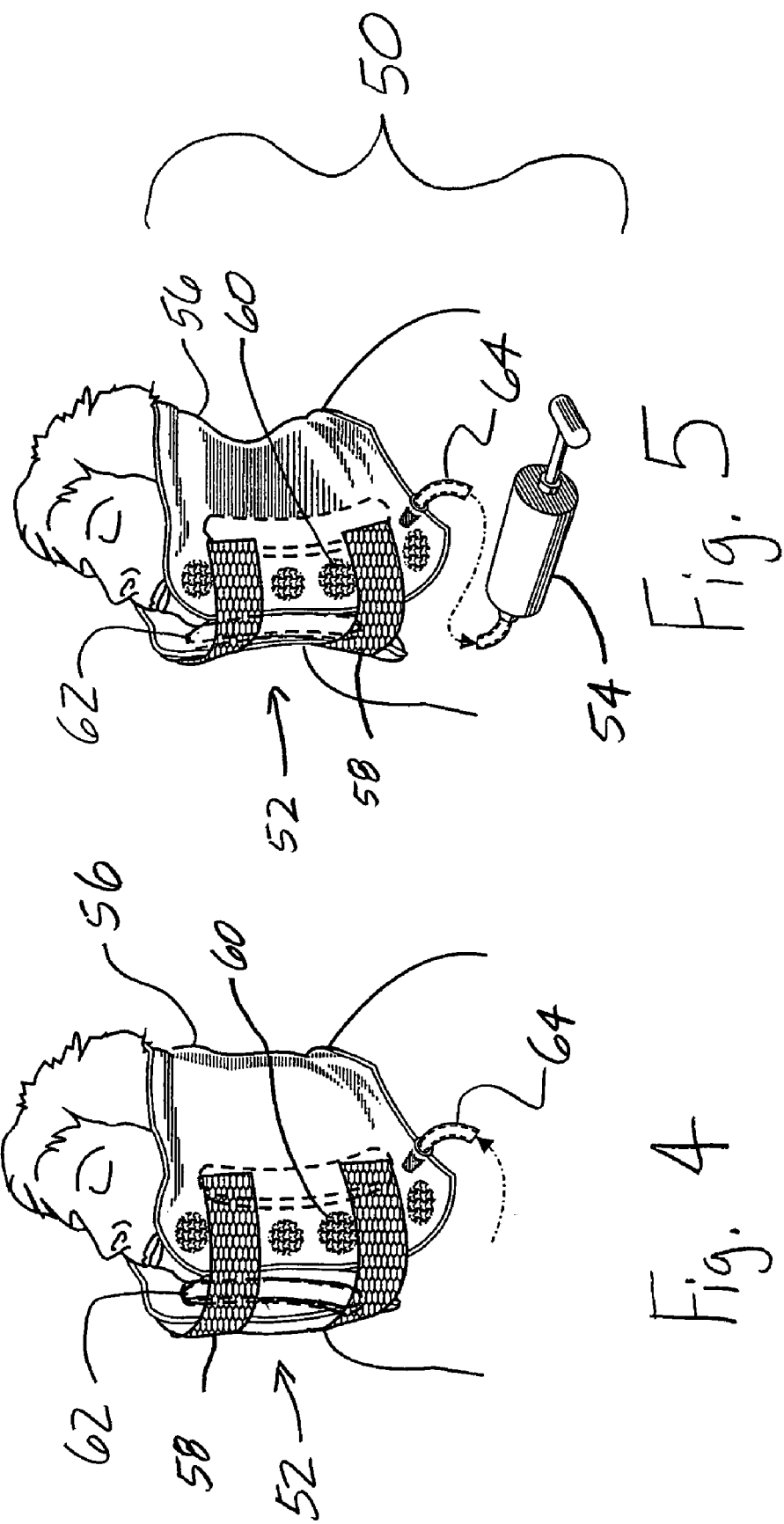

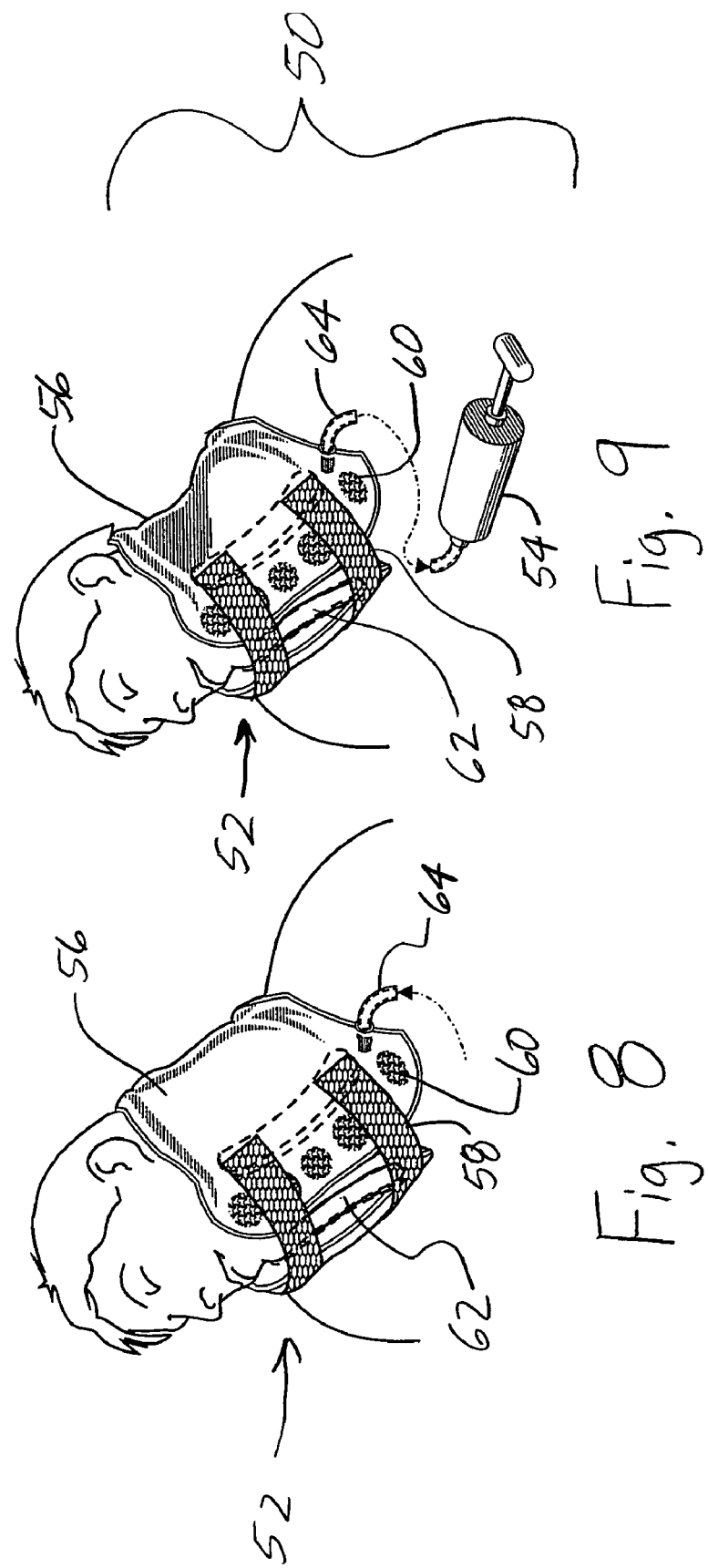

EMERGENCY MEDICAL COLLAR

CROSS-REFERENCE TO RELATED APPLICATION

None.

STATEMENT REGARDING FEDERALLY SPONSORED RESEARCH OR DEVELOPMENT

None.

BACKGROUND OF THE INVENTION

The present invention relates to emergency medical collars for immobilizing patients' necks in a variety of positions.

Before accident victims can be more fully evaluated and treated at a medical facility, they often require immobilization of part of their body before transport by emergency medical technicians (EMT's) to prevent any further injury or damage. Various forms of splinting techniques are currently used to immobilize portions of the bodies of accident victims. Included among these techniques is the use of vacuum bag/bead technology. In these devices, a bag is used that contains both air and discrete particles composed of, for example, polymers or styrofoam. With the air still in the bag, the bag is flexible and will conform to the shape of a patient it is fitted to. As air is removed from the bag, it rigidifies and provides support and/or immobilization to the part of the body it is applied to.

Conventional vacuum bags have various drawbacks impeding their use with patients who need their necks immobilized. For example, conventional vacuum bag immobilization devices are designed to splint patients with their head in only one position, generally neutral. However, EMT's may find injured people with their heads tilted in a variety of positions, including forward (flexed), back (extended), or to the side (lateral), in addition to patients whose heads are in a neutral (straight) position. It is safer to not move the patient's neck during transport, but if a patient's head is in a position other than neutral and is to be splinted in a neutral position, it is necessary to move the patient's neck before transport. Being able to immobilize a patient in whatever position (or combination of positions, or degree of position) that patient is in would increase the safety of transportation from an accident site to a hospital.

As another example of drawbacks with conventional vacuum bag immobilization devices, present designs are generally too small to encircle the neck in any position other than neutral. If such designs were enlarged, they could choke the patient when the bag were solidified if the patient were in an extended position.

It is therefore one object of the present invention to eliminate one or all of the problems associated with known emergency immobilization devices, including improving the versatility of emergency immobilization devices for immobilizing patients with neck injuries in a variety of positions.

SUMMARY OF THE INVENTION

An emergency medical collar adapted to be moved between a first more flexible state and a second more rigid state is disclosed. The emergency medical collar includes a body sized and adapted to be fitted to the neck region of a patient, and a chamber disposed inside of the body. The emergency medical collar also includes a support element disposed inside of the chamber. Further, the emergency medical collar may include a contact pad adapted for contact with a portion of a patient other than the neck. The contact pad is mounted to an exterior surface of the body. The emergency medical collar is adapted to allow attachment to the neck region of a patient when the neck of the patient is in a variety of positions, for example, neutral, extended, flexed, or lateral.

The support element of the emergency medical collar may include a plurality of beads. Also, the body of the emergency medical collar may include a first end and a second end. The emergency medical collar may also include a first contact pad mounted proximal to said first end, and a second contact pad mounted proximal to said second end. The first and second contact pads are semi-malleable and adapted to conform to a side of a patient's face. Further, the emergency medical collar may include a closable air access opening, such as a valve, mounted to the chamber to allow air to be removed from the chamber thereby moving the emergency medical collar from the first more flexible state to the second more rigid state.

BRIEF DESCRIPTION OF THE SEVERAL VIEWS OF THE DRAWINGS

FIG. 4 is an isometric view of an emergency medical collar formed in accordance with an embodiment of the present invention in a flexible position fitted to a patient's neck in an extended position.

FIG. 5 is an isometric view of the embodiment illustrated in FIG. 4 in a rigid position fitted to a patient's neck in an extended position.

FIG. 8 is an isometric view of an emergency medical collar formed in accordance with an embodiment of the present invention in a flexible position fitted to a patient's neck in a lateral position.

FIG. 9 is an isometric view of the embodiment illustrated in FIG. 8 in a rigid position fitted to a patient's neck in a lateral position.

DETAILED DESCRIPTION

Figure 1:
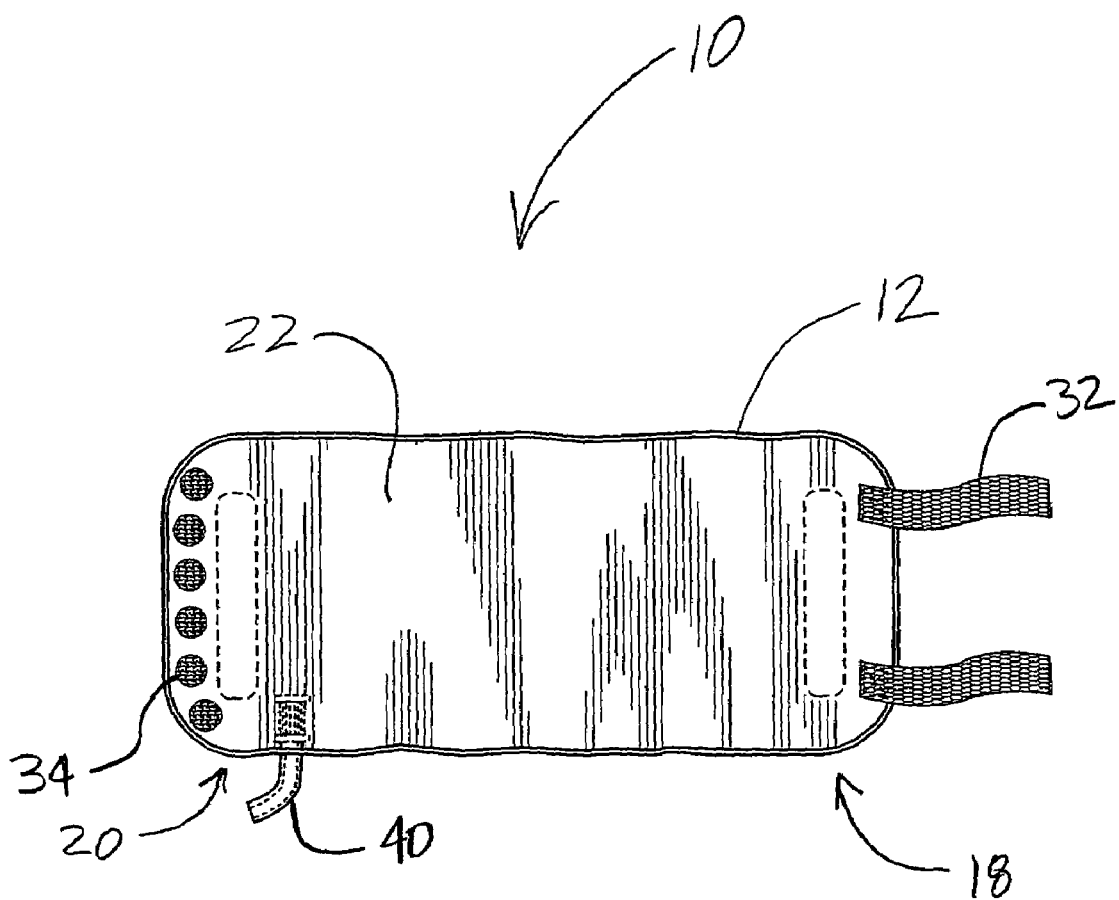
FIG. 1 is a top view of an emergency medical collar formed in accordance with an embodiment of the present invention.
Figure 2:
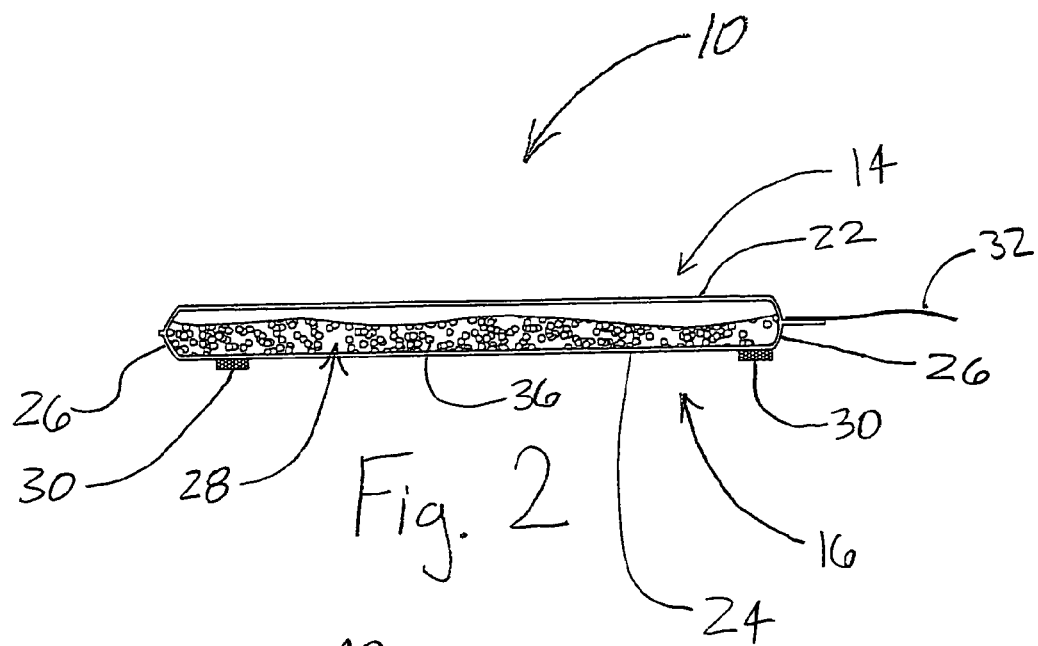
FIG. 2 is a sectional cut-away view of the embodiment illustrated in FIG. 1.
Figure 3:
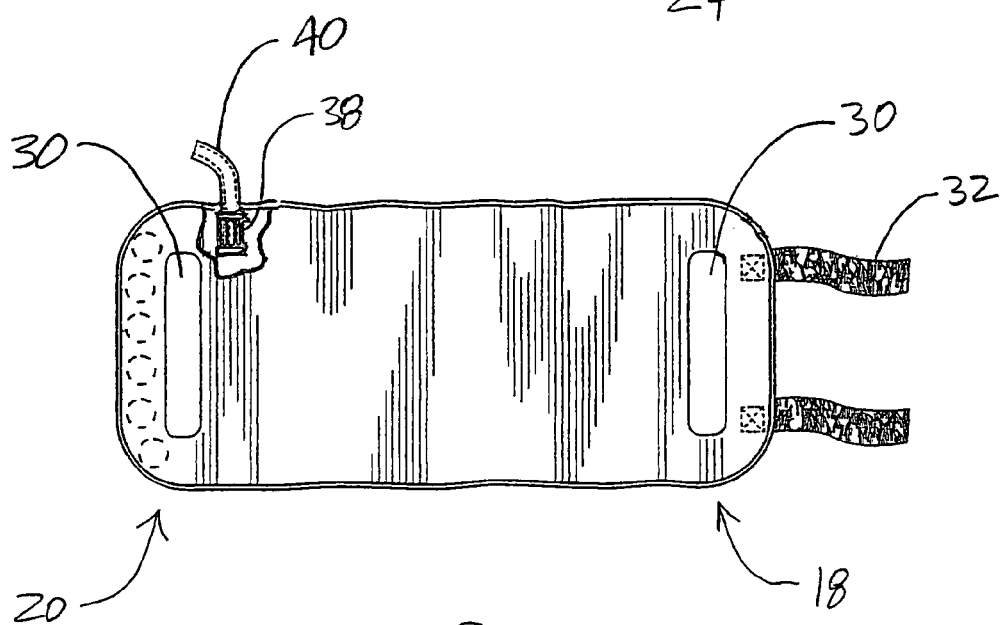
FIG. 3 is a bottom view of the embodiment illustrated in FIG. 1.

FIGS. 1-3 present different views of one embodiment of the present invention. FIG. 1 is a top view of an emergency medical collar 10 formed in accordance with an embodiment of the present invention, FIG. 2 is a sectional cut-away view of the emergency medical collar 10, and FIG. 3 is a bottom view of the emergency medical collar 10 with a portion cut away for clarity. As shown in FIGS. 1-3, the medical collar 10 includes a body 12, contact pads 30, closure elements 32 and 34, beads 36, a valve 38, and a hose 40.

The body 12 includes a top portion 14 and a bottom portion 16 joined by sides 26. The interior of the body 12 defines a cavity 28. The exterior of the body 12 is constructed and/or sealed to allow at least a partial vacuum to be maintained in the cavity 28. The sides 26 may consist of a separate piece or pieces joined to the top portion 14 and bottom portion 16, or alternatively may be defined by the joining of the top portion 14 and bottom portion 16, either as a seam or otherwise. The body 12 may be made of a polymer or copolymer. For example, the body 12 may be constructed of a polyethylene copolymer with a thickness of 0.0120 inches thick. The body 12 is generally rectangularly shaped when laid flat. The length of the body 12 is sized to allow the body 12 to be wrapped substantially around a human neck, and the width of the body 12 is sized to allow the body 12 to be in contact with at least an upper portion of a patient's torso as well as at least a lower portion of a patient's head when the emergency medical collar 10 is fitted to a patient. The body 12 includes a first end 18 and a second end 20 on opposite ends of the body 12. When the body 12 is fitted to a patient, the body 12 is wrapped around the patient's neck and the first end 18 and the second end 20 drawn toward each other to form the body 12 into a ring around a patient's neck region.

The top portion 14 of the body 12, shown facing upward in FIG. 2 and best visible in FIG. 1, faces away from a patient when the emergency medical collar 10 is fitted to a patient. The top portion 14 includes a top surface 22. When the emergency medical collar 10 is fitted to a patient, the top surface 22 faces outward. A first closure element 32 is mounted to the top surface 22 proximal to the first end 18. In the illustrated embodiment, the first closure element 32 is a strap with velcro® (a type of fastening tape utilizing nylon hooks and a nylon pile) on its underside, and two first closure elements 32 are present. A series of second closure elements 34 are mounted to the top surface 22 proximal to the second end 20. In the illustrated embodiment, these second closure elements 34 are disks with velcro® facing upward to be joined to the first closure element 32 after the emergency medical collar 10 is placed around a patient's neck. Alternatively, as an example, snaps could be used as closure elements instead of velcro®. The use of multiple second closure elements 34 provides multiple possible attachment points for the first closure elements 32 to allow for improved adjustability. The first closure element 32 and second closure element 34 cooperate to position the emergency medical collar 10 on a patient.

The bottom portion 16 of the body 12, shown facing downward in FIG. 2 and best visible in FIG. 3, faces toward the patient when the emergency medical collar 10 is fitted to a patient. The bottom portion 16 includes a bottom surface 24. Portions of the bottom surface 24 may come in contact with a patient when the emergency medical collar 10 is fitted to a patient. Contact pads 30 are mounted to bottom surface 24. As seen in FIG. 3, one contact pad 30 is mounted to the bottom surface 24 proximal to the first end 18, and another contact pad 30 is mounted to the bottom surface 24 proximal to the second end 20. The contact pad 30 is semi-malleable and adapted to conform to a patient's body and provide support when the emergency medical collar 10 is used to immobilize a patient's neck. Therefore, the contact pad 30 should be flexible enough to conform to portions of a patient's body, but rigid enough to help provide support when the emergency medical collar 10 is rigidified to prevent the collapsed emergency medical collar 10 from compressing the esophagus and choking the patient. In one embodiment of the present invention, the contact pad 30 is approximately 8" long×1½" wide by ⅜" thick, and made of high density closed cell polyethylene foam. The contact pad 30 is generally oblong, and is positioned and sized to contact at least a portion of the lower face of a patient as well as at least a portion of the upper torso of a patient when the emergency medical collar 10 is in place.

As best seen in FIG. 2, the interior of the body 12 includes a cavity 28. Beads 36 are disposed within the cavity 28. In one embodiment of the present invention, the beads 36 are approximately 1 to 3 mil in diameter. The body 12 can be also thought of as a bag that contains the beads 36, with the cavity 28 being the interior of the bag. The cavity 28 provides a chamber within which the beads 36 reside. The beads 36 are a type of support element that help give the body 12 rigidity when a quantity of air is removed from the cavity 28.

The quantity and size of the beads 36 are selected to allow the emergency medical collar 10 to be flexible when air at atmospheric pressure is present within the cavity 28 along with the beads 36, and to be rigid enough to provide adequate support to a patient when a vacuum is applied to the cavity 28. A relatively high percentage of the beads 36 can be manipulated within the cavity 28 to fill voids created by various patient head positions. The body 12 is sized to be large enough to accommodate different head positions, and is therefore relatively loose in its flexible state. Thus, the emergency medical collar 10 includes a greater volume of beads 36. For example, some conventional devices have around 150 cubic inches of beads, whereas one embodiment of the present invention has around 300 cubic inches of beads 36. When air at atmospheric pressure is present in sufficient quantities in the cavity 28, the beads 36 have enough space so that they can move relative to one another, leaving the emergency medical collar 10 in a generally flexible state in which it can be manipulated and fitted to a patient. When a vacuum is applied to the cavity 28 resulting in a removal of at least some of the air in the cavity 28, the body 12 collapses on the beads 36, reducing and/or eliminating their ability to move relative to one another, and the emergency medical collar 10 is moved to a generally rigid state in which it can support and/or immobilize a patient's neck.

As best seen in FIG. 3, the emergency medical collar 10 includes a valve 38 and a hose 40. The valve 38, when open, provides a passage for air to enter into and leave the cavity 28. The valve 38, when closed, prevents the passage of air between the cavity 28 and the atmosphere. The hose 40 is connected to the valve 38 and may be connected to a device such as a pump to aid in the application of a vacuum to the cavity 28.

FIGS. 4-8 illustrate an emergency medical collar system 50 formed in accordance with an embodiment of the present invention fitted to a patient in various states and positions. The emergency medical collar system 50 includes an emergency medical collar 52 and a pumping mechanism 54. The emergency medical collar 52 includes a bag 56, first closure element 58, second closure element 60, contact pad 62, and a hose 64. The bag 56 is sealed to be airtight, and contains beads (not shown) to provide support and rigidity when a vacuum is applied to the bag 56 and air is removed via a valve (not shown) connected to the hose 64.

FIG. 4 illustrates the emergency medical collar system 50 in a flexible state fitted to a patient's neck in an extended position, and FIG. 5 illustrates the emergency medical collar system 50 in a rigid state fitted to a patient's neck in an extended position. In FIG. 4, the valve is open, and air at atmospheric pressure is allowed into the bag 56 through the hose 64. In this state, the beads inside of the bag 56 can be manipulated and moved, making the emergency medical collar 52 flexible to allow fitting to the patient without requiring the patient's neck to be moved. As the emergency medical collar 52 is fitted around the patient's neck, beads within the bag 56 can be manipulated to fill any voids created by the position of the patient's head. As the emergency medical collar 52 continues to be fitted to the patient, the bag 56 is formed into a ring around the patient's neck, and the contact pads 62 are brought into contact with the sides of the patient's face, as well as the upper part of the patient's torso. The contact pads 62 conform to the portions of the patient's body they contact, and the first closure element 58 and the second closure element 60 are mated to secure the emergency medical collar 52 into the desired position.

The emergency medical collar 52 is now ready to be rigidified, or brought into a more rigid state, as shown in FIG. 5. This is accomplished by drawing air out of the bag 56 through the hose 64 with a pumping mechanism 54. As the air is drawn out, the bag 56 collapses around the beads and the emergency medical collar 52 stiffens. As the bag 56 collapses, the contact pads 62 prevent the bag from compressing the esophagus and choking the patient. Once enough air is drawn out of the bag 56 and the emergency medical collar 52 is rigid enough to support and/or immobilize the patient's neck, the pumping mechanism 54 is disconnected from the hose 64 and the valve is closed, maintaining the emergency medical collar 52 in its more rigid state. The patient's neck is now immobilized in the extended position the patient was initially discovered in, and the patient may be transported to a medical facility for further diagnosis and/or treatment.

Figure 7:
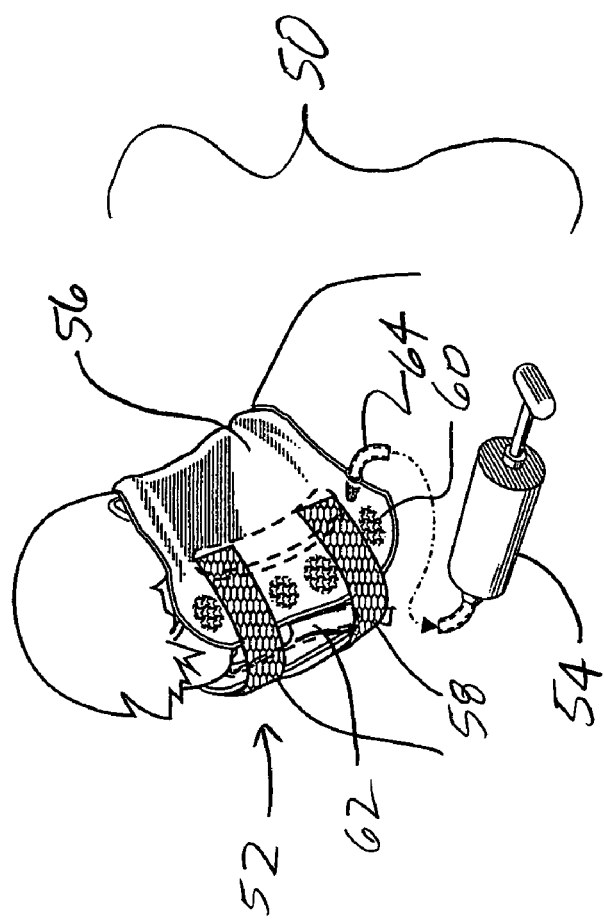
FIG. 7 is an isometric view of the embodiment illustrated in FIG. 6 in a rigid position fitted to a patient's neck in a flexed position.
Figure 6:
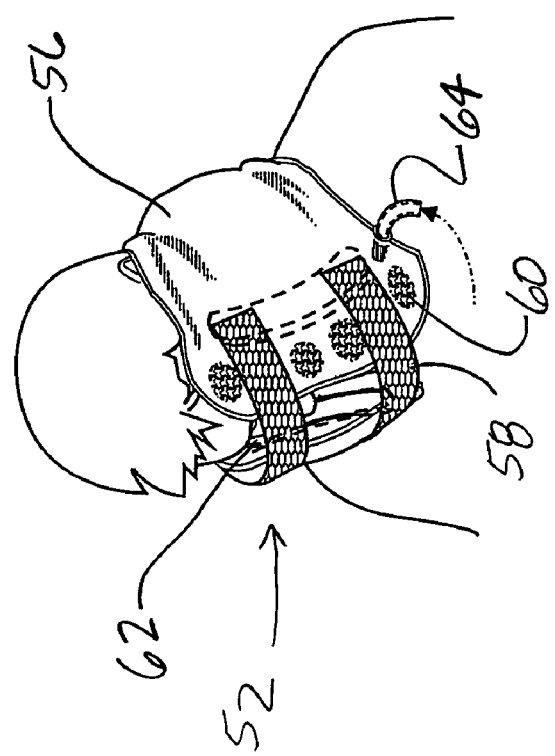
FIG. 6 is an isometric view of an emergency medical collar formed in accordance with an embodiment of the present invention in a flexible position fitted to a patient's neck in a flexed position.

FIG. 6 illustrates the emergency medical collar system 50 in a flexible state fitted to a patient's neck in a flexed position, and FIG. 7 illustrates the emergency medical collar system 50 in a rigid state fitted to a patient's neck in a flexed position. In FIG. 6, the valve is open, and air at atmospheric pressure is allowed into the bag 56 through the hose 64. In this state, the beads inside of the bag 56 can be manipulated and moved, making the emergency medical collar 52 flexible to allow fitting to the patient without requiring the patient's neck to be moved. As the emergency medical collar 52 is fitted around the patient's neck, beads within the bag 56 can be manipulated to fill any voids created by the position of the patient's head. For example, when the patient's head is in a flexed position, a void is created behind the patient's neck, and the beads may be manipulated to fill that void. As the emergency medical collar 52 continues to be fitted to the patient, the bag 56 is formed into a ring around the patient's neck, and the contact pads 62 are brought into contact with the sides of the patient's face, as well as the upper part of the patient's torso. The contact pads 62 conform to the portions of the patient's body they contact, and the first closure element 58 and the second closure element 60 are mated to secure the emergency medical collar 52 into the desired position.

The emergency medical collar 52 is now ready to be rigidified, or brought into a more rigid state, as shown in FIG. 7. This is accomplished by drawing air out of the bag 56 through the hose 64 with a pumping mechanism 54. As the air is drawn out, the bag 56 collapses around the beads and the emergency medical collar 52 stiffens. As the bag 56 collapses, the contact pads 62 prevent the bag from compressing the esophagus and choking the patient. Once enough air is drawn out of the bag 56 and the emergency medical collar 52 is rigid enough to support and/or immobilize the patient's neck, the pumping mechanism 54 is disconnected from the hose 64 and the valve is closed, maintaining the emergency medical collar 52 in its more rigid state. The patient's neck is now immobilized in the flexed position the patient was initially discovered in, and the patient may be transported to a medical facility for further diagnosis and/or treatment.

FIG. 8 illustrates the emergency medical collar system 50 in a flexible state fitted to a patient's neck in a lateral position, and FIG. 9 illustrates the emergency medical collar system 50 in a rigid state fitted to a patient's neck in a lateral position. In FIG. 8, the valve is open, and air at atmospheric pressure is allowed into the bag 56 through the hose 64. In this state, the beads inside of the bag 56 can be manipulated and moved, making the emergency medical collar 52 flexible to allow fitting to the patient without requiring the patient's neck to be moved. As the emergency medical collar 52 is fitted around the patient's neck, beads within the bag 56 can be manipulated to fill any voids created by the position of the patient's head. For example, when the patient's head is in a lateral position, a void is created to the side of the patient's neck, and the beads may be manipulated to fill that void. As the emergency medical collar 52 continues to be fitted to the patient, the bag 56 is formed into a ring around the patient's neck, and the contact pads 62 are brought into contact with the sides of the patient's face, as well as the upper part of the patient's torso. The contact pads 62 conform to the portions of the patient's body they contact, and the first closure element 58 and the second closure element 60 are mated to secure the emergency medical collar 52 into the desired position.

The emergency medical collar 52 is now ready to be rigidified, or brought into a more rigid state, as shown in FIG. 9. This is accomplished by drawing air out of the bag 56 through the hose 64 with a pumping mechanism 54. As the air is drawn out, the bag 56 collapses around the beads and the emergency medical collar 52 stiffens. As the bag 56 collapses, the contact pads 62 prevent the bag from compressing the esophagus and choking the patient. Once enough air is drawn out of the bag 56 and the emergency medical collar 52 is rigid enough to support and/or immobilize the patient's neck, the pumping mechanism 54 is disconnected from the hose 64 and the valve is closed, maintaining the emergency medical collar 52 in its more rigid state. The patient's neck is now immobilized in the lateral position the patient was initially discovered in, and the patient may be transported to a medical facility for further diagnosis and/or treatment.

Thus, the emergency medical collar system 50 can be fitted to patients in various head and neck positions, without the patient's neck having to be moved before immobilization. Additionally, the emergency medical collar system 50 can be adjusted to account for additionally positions not illustrated, such as for combinations of positions or varying degrees of extension or flexion.

While particular embodiments of the invention have been shown, it will be understood that the invention is not limited thereto since modifications may be made by those skilled in the art, particularly in light of the foregoing teaching. For example, different shapes and/or quantities and/or locations of contact pads may be used. For instance, instead of using one contact pad on each end of the collar, each end of the collar could have two separate contact pads, one designed to conform to the patient's head/face and the other to conform to the patient's torso. As another example, different types and/or quantities and/or locations of closure elements may be used. It is therefore, the appended claims that define the true spirit and scope of the invention.

What is claimed is:

1. An emergency medical collar adapted to be movable between a first more flexible state and a second more rigid state comprising
    a body sized and adapted to be fitted to the neck region of a patient;
    a chamber disposed inside of said body;
    a support element disposed inside of said chamber; and,
    at least one semi-malleable contact pad adapted for contact with a portion of a patient other than the neck, said contact pad mounted to and extending from only a portion of an exterior surface of said body,
wherein said emergency medical collar is adapted to allow attachment to the neck region of a patient when the neck of the patient is in a variety of positions.

2. The emergency medical collar of claim 1 wherein said variety of patient neck positions said emergency medical collar is adapted to allow attachment to include a flexed position, a lateral position, and an extended position.

3. The emergency medical collar of claim 1 wherein said support element comprises a plurality of beads.

4. The emergency medical collar of claim 1 comprising a first semi-malleable contact pad mounted proximal to a first end and a second semi-malleable contact pad mounted proximal to an opposite ends of said body.

5. The emergency medical collar of claim 1 further comprising a closable air access opening mounted to said chamber adapted to allow air to be removed from said chamber thereby moving said emergency medical collar from said first more flexible state to said second more rigid state.

6. An emergency medical collar comprising
    a bag sized and adapted to be fitted to the neck region of a patient in a variety of positions, said bag having a first end and a second end;
    a plurality of support elements disposed inside of said bag, said support elements sized and in a quantity adapted to allow manipulation of said support elements inside of said bag such that said bag may be fitted to a plurality of neck positions, said support elements adapted to cooperate with the amount of air in said bag to allow said medical collar to move from a first more flexible state to a second more rigid state when air is removed from said bag;
    a at least one semi-malleable contact pad adapted for contact with a portion of a patient other than the neck mounted to and extending from only a portion of an exterior surface of said bag;
    closure elements attached to said first and second ends of said bag, said closure elements adapted to cooperate to position said bag; and,
    a valve attached to said bag to allow control of the amount of air in said bag.

7. The emergency medical collar of claim 6 wherein said plurality of support elements has a volume of at least approximately 300 cubic inches.

8. The emergency medical collar of claim 6 wherein said plurality of support elements comprises beads having a diameter between approximately 1 mil and approximately 3 mil.

9. The emergency medical collar of claim 6 further comprising a plurality of semi-malleable contact pads adapted for contact with a portion of a patient other than the neck.

10. The emergency medical collar of claim 6 further comprising a first semi-malleable contact pad mounted proximal to said first end of said bag and a second semi-malleable contact pad mounted proximal to said second end of said bag.

11. An emergency medical collar comprising
    a body sized and adapted to be fitted to the neck region of a patient in a variety of positions, said body having a top portion and a bottom portion joined by sides, said body being generally rectangular shaped and having a first end and a second end opposite said first end when said body lies generally flat, said first and second ends being located proximal to each other when said body is fitted to the neck region of a patient;
    a cavity defined by said top portion, bottom portion, and sides;
    a plurality of support elements disposed inside of said cavity, said support elements sized and in a quantity adapted to allow manipulation of said support elements inside of said cavity such that said bag may be fitted to a plurality of neck positions, said support elements adapted to cooperate with the amount of air in said cavity to allow said medical collar to move from a first more flexible state to a second more rigid state when air is removed from said cavity;
    a valve attached to said cavity to allow control of the amount of air in said cavity;
    a semi-malleable contact pad mounted to and extending from only a portion of said bottom portion of said body, said contact pad adapted for contact with a portion of a patient other than the neck;
    a first closure element mounted to said top portion of said body proximal to said first end; and,
    a second closure element mounted to said top portion of said body proximal to said second end, said first and second closure elements adapted to cooperate to position said body.

12. The emergency medical collar of claim 11 wherein said plurality of support elements has a volume of at least approximately 300 cubic inches.

13. The emergency medical collar of claim 11 wherein said plurality of support elements comprise beads having a diameter between approximately 1 mil and approximately 3 mil.

* * * * *